United States Patent [19]

Martin

[11] 3,992,362

[45] Nov. 16, 1976

[54] FRIABLE TERTIARY AMYL PHENOL SULFIDES AS VULCANIZING AGENT

[75] Inventor: Le Roy Martin, Riverview, Mich.

[73] Assignee: Pennwalt Corporation, Philadelphia, Pa.

[22] Filed: Aug. 14, 1975

[21] Appl. No.: 604,584

Related U.S. Application Data

[62] Division of Ser. No. 432,257, Jan., 1974.

[52] U.S. Cl. .................... 260/79.5 C; 260/23.7 B; 260/23.7 M; 260/79.5 R; 260/79.5 P; 260/79.5 B; 260/775
[51] Int. Cl.² .................... C08F 28/00; C08G 75/14
[58] Field of Search ................ 260/48, 137, 79.5 R, 260/79.5 P, 79.5 B, 79.5 C, 775

[56] References Cited
UNITED STATES PATENTS

| | | | |
|---|---|---|---|
| 1,849,489 | 3/1932 | Howland | 260/48 |
| 2,175,082 | 10/1939 | Hagen et al. | 260/45.95 C |
| 2,422,156 | 6/1947 | Wolf et al. | 260/79.5 R |
| 3,406,158 | 10/1968 | Brown et al. | 260/137 |
| 3,455,851 | 7/1969 | Meredith et al. | 260/48 |
| 3,498,936 | 3/1970 | Wilson | 260/48 |
| 3,919,171 | 11/1975 | Martin | 260/48 |

*Primary Examiner*—Ronald W. Griffin
*Attorney, Agent, or Firm*—Robert G. Danehower

[57] ABSTRACT

Tertiary amyl phenol sulfides are made in flaked form by reacting tertiary amyl phenol with sulfur monochloride at a mole ratio of 0.7 to 0.95 moles of the phenol to one mole of sulfur monochloride. The hot liquid reaction product is then flaked on a cooled surface. The use of tertiary amyl phenol sulfides as a sulfur donor in the vulcanization of rubber is facilitated by its ease of shipping and handling in flaked form.

4 Claims, No Drawings

FRIABLE TERTIARY AMYL PHENOL SULFIDES AS VULCANIZING AGENT

This is a division of application Ser. No. 432,257, filed Jan. 10, 1974, now U.S. Pat. No. 3,919,171, issued Nov. 11, 1975.

BACKGROUND OF THE INVENTION

Tertiary amyl phenol sulfides have been widely used as sulfur donors in the vulcanization of sulfur curable rubber for many years. Millions of pounds of this material have been supplied to the rubber industry in fiber or steel drums. As presently known in the industry, this material is sold in the form of a solid tacky chunk. When the rubber formulator wants to use this large chunk of tacky material in compounding rubber, he has a choice of either chopping up the fiber board drum with an axe or else of heating the metal drum of tertiary amyl phenol sulfides in a heated bath and pouring off the melted sulfides as needed. Either method of handling the sulfides is expensive, time consuming, wasteful and leaves the work area in a dirty condition.

When a fiber drum of tertiary amyl phenol sulfide is chopped with an axe, the sulfide will scatter over the work area, and since it is quite tacky, it will adhere to the floor as well as to the workers shoes. As the residue builds up on the floor a dirty and dangerous condition in the work area is created. When tertiary amyl phenol sulfides are shipped in metal drums (approximately 325 pounds net weight) the tacky glob must be heated to melt the sulfides to the liquid form before they can be used in small quantities in compounding the rubber. Extended heating and holding the sulfide in the molten state causes thermal degradation of the product and discoloration.

The tacky nature of the tertiary amyl phenol sulfides as used in the rubber industry up to the time of my invention was recognized in U.S. Pat. No. 2,422,156 wherein a mole ratio of two moles of tertiary amyl phenol to one mole of sulfur monochloride is disclosed. This patent also discloses the use of tertiary amyl phenol sulfides as a vulcanization agent (sulfur donor) for rubber and the disclosure of this patent is incorporated herein by reference.

Commercial products of para tertiary amyl phenol sulfides and polysulfides have been supplied to the rubber industry up to the present time in which the mole ratio of para tertiary amyl phenol to sulfur monochloride has ranged from 2 to 1 to 1 to 1. All of these products have been quite tacky and difficult to remove from the shipping containers.

Various additives have been incorporated in para tertiary amyl phenol sulfides when they are used as vulcanization agents. Industrial White oil in small quantities has been used in commercial products. Large amounts of stearic acid (up to 35% by weight) and oleic acid (45% by weight) have also been used but with little success. Adding up to 25% by weight of a diatomaceous earth has provided a free flowing granular product but it is an expensive diluent and is also a contaminant in the rubber when it is vulcanized.

SUMMARY OF INVENTION

In accordance with this invention para tertiary amyl phenol sulfides are produced by a process that permits the product to be flaked or ground for convenient packaging and dispensing from the shipping container. Moreover, the flaked or ground product does not coalesce during long storage periods. The term friable is used to describe these products which are capable of being ground at ambient temperature and which do not coalesce at ambient temperature.

In my improved process which produces a friable product an excess of sulfur monochloride is added as rapidly as possible to molten para tertiary amyl phenol and the temperature allowed to rise preferably within the range of 160° to 190° C. After the hydrogen chloride has been liberated the molten reaction product is dropped onto a granulating apparatus, such as a flaking belt or drum and the granulated product is then discharged into shipping drums. If desired, the product can be ground into finer sizes by conventional grinding apparatus such as a hammer mill. The mole ratio of the reactants as well as the residence time in the reactor are important in obtaining a granular product.

DETAILED DESCRIPTION OF THE INVENTION

In the production of friable para tertiary amyl phenol sulfides in granular or flaked form para tertiary amyl phenol is added to a mixing vessel equipped with mechanical agitation and heat exchanges means such as a jacketed reactor. The alkyl phenol is either introduced to the reactor in a molten condition or else it is introduced as a solid and then melted or at least partially melted by means of the heat exchanger before sulfur monochloride addition is started.

Since hydrogen chloride gas is evolved suitable reactor materials such as glass must be used. Also, since the reaction between sulfur monochloride and the para tertiary amyl phenol is quite exothermic, cooling means should be available to the reactor.

Sulfur monochloride which is a pungent liquid is then introduced as quickly as possible with agitation but at a rate which does not let the reaction temperature exceed about 200° C. Preferably the reaction temperature is maintained within the range of about 160° to about 190° C. Since high temperatures discolor and thermally degrade para tertiary amyl phenol sulfides, the $S_2Cl_2$ is added to the para tertiary amyl phenol as quickly as the reaction temperature permits. Since the reaction is quite exothermic, use of external cooling facilitates rapid addition of the $S_2Cl_2$.

The mole ratio of para tertiary amyl phenol to sulfur monochloride is critical in my process and must be within the range of about 0.7 to about 0.95 to 1, and preferably the mole ratio is about 0.9 to 1, thus ensuring an excess of sulfur monochloride.

The lower the mole ratio of para tertiary amyl phenol to $S_2Cl_2$ the more viscous is the liquid reaction product and accordingly, a greater degree of friability in the product when cooled to ambient temperature. When a mole ratio of 0.7 to 1 is used the reaction product is quite viscous, even at 200° C. and should be removed as quickly as possible from the reactor.

Hydrogen chloride is evolved continuously from the reaction mass and must be conducted to a recovery system or scrubbed with an alkali.

The softening point is an index of the friability of the para tertiary amyl phenol sulfide product and the softening point is inversely proportinal to the mole ratio of para tertiary amyl phenol to $S_2Cl_2$.

| Mole Ratio - | PTAP S₂Cl₂ | Softening Point of Product (° C) |
|---|---|---|
| | 1.33 | 50–60 |
| | 1.10 | 65–75 |
| | 1.00 | 78–93 |
| | 0.90 | 118–128 |

Softening points were determined by the A.S.T.M. Ring-Ball apparatus E-28.

After all of the sulfur monochloride has been added and hydrogen chloride has stopped evolving, the molten product is then purged of dissolved hydrogen chloride. This may be done by passing an inert gas such as dry air or nitrogen through the molten product, or by reducing the pressure on the reactor until nearly all of the hydrogen chloride is removed. To test the completion of hydrogen chloride removal, the product should be analyzed for free HCl which should not exceed 0.1% by weight at the finish. The hydrogen chloride removal can also be followed by testing the effluent gas stream which should be neutral to litmus or pH paper at the completion.

After liberation of the hydrogen chloride the liquid para tertiary amyl phenol sulfides are discharged as quickly as possible. Preferably, the liquid reaction product is discharged onto a granulating apparatus. Such apparatus could be a granulator or flaking apparatus such as a moving belt flaker or a drum flaker. Cooling means in the granulating apparatus facilitates the cooling of the molten para tertiary amyl phenol sulfides and thereby increase the through-put of the granulating apparatus.

If the liquid reaction is extremely viscous, or if it is preferred for any reason, the molten product can be introduced directly into shipping drums where it will solidify into a solid chunk. When this friable product is removed from a drum as by cracking it, the pieces remain quite crystalline and do not adhere to the floor or clothing of the operators as was the case with the product made with the prior art mole ratios.

The liquid reaction product can also be cast into molds and allowed to cool and crystallize before being discharged from the molds. After cooling, the product can be ground in conventional grinding equipment.

The para tertiary amyl phenol sulfides prepared as described above are amber to brown in color and contain about 29.8 percent sulfur by weight when the mole ratio of para tertiary amyl phenol to S₂ to Cl₂ is 0.9. As the mole ratio decreases the sulfur content increases slightly. The flakes of para tertiary amyl phenol sulfides are stable to heat and do not coalesce at temperatures up to 125° F. This is considered a safe temperature for shipping and storage in the U.S.

The exact chemical structure of the sulfides produced by my process are not known. The various chemical structures which can be produced by the reaction are postulated in U.S. Pat. No. 2,422,156. It is likely that the friable product of this reaction is a mixture of these various structures and accordingly it is referred to as para tertiary amyl phenol sulfides.

Para tertiary amyl phenol sulfides are vulcanization agents for sulfur curable polymers such as styrene-butadiene copolymer, chlorobutyl rubber, natural rubber and ethylene-propylene diene copolymer. The para tertiary amyl phenol sulfides can be used as the sole vulcanization agent or it can be used in conjunction with other sulfur donors.

The best mode of making and using my invention will be apparent from a consideration of the following examples:

EXAMPLE 1

Into a one liter 3-necked flask fitted with mechanical agitation, thermowell, and addition tube 1.9 gram moles of p-tertiary amyl phenol was charged. Sulfur monochloride (2.0 moles) was added over a period of 45 minutes while liberating hydrogen chloride. At the end of the addition period the exotherm had reached a temperature of 160° C. After aeration to liberate the gas the product was discharged onto a flaker. Xray diffraction showed that the product was amorphous.

EXAMPLE 2

The process of Example 1 was repeated except that 2.2 moles of para tertiary amyl phenol was charged to the flask and 2 moles of S₂Cl₂ added over a period of about 1 hour. The reaction product had a set point of about 70° C. and was too tacky to flake.

EXAMPLE 3

Using the procedure of Example 1, 0.7 moles of para tertiary amyl phenol was charged to the reaction flask and 1 mole of S₂Cl₂ added over a period of about forty minutes. At the completion of the S₂Cl₂ addition, the reaction product was quite viscous even at a temperature of 200° C. The product was quite friable.

EXAMPLE 4

Into a 1,000 gallon glass-lined reactor, 2,068 pounds of para tertiary amyl phenol was added. This material was partially melted and 1,900 pounds of sulfur monochloride was added at such a rate that at the end of addition the reaction temperature was 180°–190° C. The mole ratio of para tertiary amyl phenol to sulfur monochloride was 0.9 to 1. The time of addition was 3.5–4 hours. After aeration for about 30 minutes to eliminate residual hydrogen chloride, the product was dropped to a belt flaker and flaked. The softening point of several batches averaged about 120° C.

The above production runs were repeated except that the product temperature at the completion of the S₂Cl₂ addition were 194° C., 185° C., and 173° C. and 160° C. respectively. The reaction product was friable in every case.

EXAMPLE 5

The procedure of Example 4 was repeated except that 1,900 pounds of S₂Cl₂ were added to 2,191 pounds of para tertiary amyl phenol, giving a mole ratio of para tertiary amyl phenol/S₂Cl₂ of 0.95/1. The product para tertiary amyl phenol sulfides were packaged directly into drums. Several pounds of the product were flaked on a steel belt.

EXAMPLE 6

The procedure of Example 4 was repeated using 1,900 pounds of S₂Cl₂ and 2,361 pounds of para tertiary amyl phenol giving a mole ratio of 1/1. The product had a softening point within the range of 78 to 93° C. It was discharged directly into drums.

EXAMPLE 7

A batch of para tertiary amyl phenol sulfide made according to Example 4 was discharged onto a Sandvik belt flaker travelling at 36 ft./min. with a surface area of 16 sq. ft. The temperature of the product in the reactor was in the range of 160° to 180° C at the time of discharge to the flaker. In order to discharge the reactor it was placed under a pressure of 30 to 40 p.s.i.g. with air.

The flakes of para tertiary amyl phenol sulfides broke off of the belt of their own weight and it was unnecessary to use a knife edge. Flaking rates averaged between 40 and 42 pounds per hour per square foot. Some curling up of the flakes on the belt was observed.

EXAMPLE 8

Para tertiary amyl phenol sulfides produced at mole ratios of 0.8, 0.9, 0.95 and 1.0 of para tertiary amyl phenol to $S_2Cl_2$ were flaked on a steel belt and samples placed in a circulating air oven held at 125° C. Over a six month observation period the flaked products produced at mole ratios of 0.8 to 0.9 and 0.95 had not coalesced. The product with the mole ratio of 1.0 coalesced within 24 hours at this temperature.

EXAMPLE 9

Rubber compounding tests have indicated that this process produces para tertiary amyl phenol sulfide which is a vulcanization agent that is equal or superior in performance to the product prepared by the previous processes where the mole ratio of para tertiary amyl phenol to sulfur monochloride was one to one or greater than one to one.

A rubber mixture was compounded on rubber mill rolls in the usual manner, containing the following constituents (parts by weight):

| | |
|---|---|
| Styrene - butadiene copolymer 1606 | 162.0 |
| Zinc oxide | 5.0 |
| Stearic Acid | 2.0 |
| 2-Benzothiazyl)-N,N-Diethyldithiocarbamate | 1.0 |

100 parts by weight of the above rubber mixture was compounded with 4.2 parts by weight of para tertiary amyl phenol sulfide made from reaction mixtures having varying mole ratios of para tertiary amyl phenol (PTAP) to sulfur monochloride ($S_2Cl_2$). The rubber was then vulcanized at 320° F. for varying time periods. The properties of the vulcanizates are shown in Table I below. The Vultac 3 sample represents a presently commercially available para tertiary amyl phenol polysulfide vulcanization agent containing about 3% by weight of Industrial White oil. The mole ratio of PTAP to $S_2Cl_2$ of this product is about 1.

Table I

| Curing Time (Minutes) | Vultac 3 | Mole Ratio - (TAP/$S_2Cl_2$) 1.0 | 0.95 | 0.90 | 0.80 |
|---|---|---|---|---|---|
| | | 300% Modulus (lbs/in²) | | | |
| 10 | 450 | 625 | 560 | 575 | 610 |
| 20 | 700 | 910 | 900 | 890 | 1060 |
| 30 | 740 | 1010 | 1030 | 940 | 1225 |
| 40 | 850 | 1050 | 1010 | 1050 | 1220 |
| 60 | 825 | 1070 | 1090 | 1000 | 1300 |
| | | Tensile Strength (lbs/in²) | | | |
| 10 | 1580 | 2160 | 2200 | 2150 | 2175 |

Table I-continued

| | Vultac 3 | Mole Ratio - (TAP/$S_2Cl_2$) 1.0 | 0.95 | 0.90 | 0.80 |
|---|---|---|---|---|---|
| 20 | 2575 | 3100 | 3000 | 3020 | 3100 |
| 30 | 2700 | 3160 | 3075 | 3160 | 3450 |
| 40 | 2775 | 3200 | 3030 | 3225 | 3450 |
| 60 | 2800 | 3320 | 3120 | 2970 | 3700 |
| | | Elongation (%) | | | |
| 10 | 850 | 810 | 850 | 850 | 800 |
| 20 | 810 | 750 | 750 | 800 | 710 |
| 30 | 770 | 710 | 690 | 750 | 690 |
| 40 | 780 | 660 | 690 | 750 | 650 |
| 60 | 730 | 680 | 650 | 660 | 660 |
| | | Hardness-Shore-A Durometer | | | |
| 10 | 61 | 62 | 62 | 62 | 61 |
| 20 | 61 | 63 | 63 | 63 | 63 |
| 30 | 62 | 63 | 64 | 63 | 63 |
| 40 | 62 | 65 | 64 | 64 | 63 |
| 60 | 62 | 65 | 64 | 64 | 64 |
| | | Mooney Scorch at 266° F (minutes) | | | |
| | 21 | 21 | 20 | 19 | 21 |

I claim:
1. In the manufacture of a vulcaized elastomeric product, the process which comprises mixing 100 parts by weight of a sulfur curable vulcanizable polymerizate selected from the group consisting essentially of styrene-butadiene copolymer, chlorobutyl rubber, natural rubber and ethylene-propylene diene copolymer with about 5 to 25 parts by weight of para tertiary amyl phenol sulfides having a softening point of at least 118° C. and thereafter vulcanizing the mixture.

2. In the manufacture of a vulcanized elastomeric product, the process which comprises mixing 100 parts by weight of a sulfur curable vulcanizable polymerizable selected from the group consisting essentially of styrene-butadiene copolymer, chlorobutyl rubber, natural rubber and ethylene-propylene diene copolymer with about 5 to 25 parts by weight of para tertiary amyl phenol sulfides manufactured by introducing sulfur monochloride to molten para tertiary amyl phenol in a reactor at a mole ratio of the said phenol to sulfur monochloride within the range of 0.7 to 0.95 to 1 while agitating the reaction mixture,
adding the said sulfur monochloride to the reaction mixture as fast as possible but at a rate which prevents the exothermic reaction from exceeding the maximum temperature of 200° C.,
continuously venting hydrogen chloride from the reactor as it evolves from the liquid reaction mixture until the reaction is complete, and finally
discharging friable para tertiary amyl phenol sulfides from the reactor, and thereafter vulcanizing the mixture.

3. A vulcanized elastomer obtained by mixing 100 parts by weight of a sulfur curable vulcanizable polymerizate selected from the group consisting essentially of styrene-butadiene copolymer, chlorobutyl rubber, natural rubber and ethylene-propylene diene copolymer with about 5 to about 25 parts by weight of para tertiary amyl phenol sulfides manufactured by introducing sulfur monochloride to molten para tertiary amyl phenol in a reactor at a mole ratio of the said phenol to sulfur monochloride within the range of 0.7 to 0.95 to 1 while agitating the reaction mixture,
adding the said sulfur monochloride to the reaction mixture as fast as possible but at a rate which prevents the exothermic reaction from exceeding the maximum temperature of 200° C., continuously venting hydrogen chloride from the reactor as it evolves from the liquid reaction mixture until the reaction is complete, and finally discharging friable para tertiary amyl phenol sulfides from the reactor, and thereafter vulcanizing the mixture.

4. A vulcanized elastomer obtained by mixing 100 parts by weight of a sulfur curable vulcanizable polymerizate selected from the group consisting essentially of styrene-butadiene copolymer, chlorobutyl rubber, natural rubber and ethylene-propylene diene copolymer with about 5 to about 25 parts by weight of para tertiary amyl phenol sulfides having a softening point of at least 118° C. and thereafter vulcanizing the mixture.

* * * * *